United States Patent
de Lumen et al.

(10) Patent No.: US 7,375,092 B2
(45) Date of Patent: *May 20, 2008

(54) LUNASIN PEPTIDES

(75) Inventors: Benito O. de Lumen, Berkeley, CA (US); Alfredo F. Galvez, Berkeley, CA (US)

(73) Assignee: Regents of the University of California, Oakland, CA (US)

( * ) Notice: Subject to any disclaimer, the term of this patent is extended or adjusted under 35 U.S.C. 154(b) by 1159 days.

This patent is subject to a terminal disclaimer.

(21) Appl. No.: 10/302,633

(22) Filed: Nov. 22, 2002

(65) Prior Publication Data

US 2003/0229038 A1    Dec. 11, 2003

Related U.S. Application Data

(63) Continuation of application No. 09/531,727, filed on Mar. 21, 2000, now Pat. No. 6,544,956, which is a continuation of application No. 08/938,675, filed on Sep. 25, 1997, now Pat. No. 6,107,287.

(51) Int. Cl.
*A61K 31/70* (2006.01)
*C12N 1/20* (2006.01)
*C12N 5/10* (2006.01)
*C12N 5/02* (2006.01)

(52) U.S. Cl. .................. 514/44; 435/455; 435/375; 435/325

(58) Field of Classification Search ............. 514/44; 435/455, 375, 325

See application file for complete search history.

(56) References Cited

U.S. PATENT DOCUMENTS

| 5,494,806 | A | | 2/1996 | Segre et al. |
| 5,594,120 | A | | 1/1997 | Brenner et al. |
| 5,726,018 | A | | 3/1998 | Pasternack |
| 5,770,422 | A | | 6/1998 | Collins |
| 5,850,016 | A | | 12/1998 | Jung et al. |
| 6,020,202 | A | | 2/2000 | Jessee |
| 6,090,577 | A | * | 7/2000 | Hillman et al. ............ 435/69.1 |

OTHER PUBLICATIONS

Sryer L., in Prediction of Conformation From Amino Acid Sequenced. Biochemistry. 1975, W. H. Freeman and Company, New York, p. 37.*

* cited by examiner

*Primary Examiner*—Anne Marie S. Wehbe
*Assistant Examiner*—Maria Leavitt
(74) *Attorney, Agent, or Firm*—Richard Aron Osman

(57) ABSTRACT

The invention provides methods and compositions of selectively disrupting mitotic function in a target cell demonstrating undesirable mitotic function. Suitable target cells include mammalian, plant and bacterial cells, which cells may be in vitro or in situ. The general methods involve introducing into the target cell an effective amount of a peptide comprising contiguous acidic amino acids, such as Asp or Glu, whereby the undesirable mitotic function of the cell is selectively disrupted. In particular embodiments, the peptide comprises a Gm2S-1 peptide, particularly a lunasin and/or alisin peptide. The peptide may be introduced by transfecting the cell with a nucleic acid encoding the peptide.

22 Claims, No Drawings

LUNASIN PEPTIDES

CROSS-REFERENCE TO RELATED APPLICATION

This application is a continuation of and claims priority under 35 U.S.C § 120 to U.S. application Ser. No. 09/531,727, filed Mar. 21, 2000, now U.S. Pat. No. 6,544,956, which is a continuation of and claims priority to U.S. application Ser. No. 08/938,675, filed Sep. 25, 1997, now U.S. Pat. No. 6,107,287, which we incorporated herein by reference.

The research carried out in the subject application was supported in part by USDA NRICGP Grant # 94-02167. The government may have rights in any patent issuing on this application.

INTRODUCTION

1. Field of the Invention

The invention relates to a class of peptides which disrupts mitotic function in cells.

2. Background of the Invention

Early seed development in angiosperms is characterized by rapid cell division and differentiation followed by cessation of cell division and the start of cell expansion during which DNA endoreduplication and massive synthesis of storage proteins, carbohydrates and lipids occur in the endosperm of cereals and in the cotyledons of legumes (1). The molecular mechanisms underlying these early events are poorly understood. The temporal expression of 2S albumins, a diverse group of water soluble proteins found in developing seeds, has been shown to coincide with the initiation of cell expansion after the cells stopped dividing in developing pea embryos (2). In situ hybridization work on Arabidopsis involving actively dividing and nondividing parynchema cells also suggests the possible existence of a regulatory mechanism that is common to 2S albumin gene expression and mitotic activity (3). However, the functional role of 2S albumins in regulation of mitosis during seed development remains to be established.

SUMMARY OF THE INVENTION

The invention provides methods and compositions of selectively modulating mitotic function in a target cell demonstrating undesirable mitotic function. Suitable target cells include mammalian, plant and bacterial cells, which cells may be in vitro or in situ. The general methods involve introducing into the target cell an effective amount of a modulator of mitotic function comprising a Gm2S-1 peptide and/or contiguous acidic amino acids, such as Asp or Glu, whereby the undesirable mitotic function of the cell is selectively modulated. In particular embodiments, the Gm2S-1 peptide comprises the contiguous acidic amino acids and/or comprises residues 33-43, residues 85-91, residues 123-127, residues 85-127, at least 12 contiguous residues of SEQ ID NO:2, residues 1-35 and/or SEQ ID NO:2. The peptide may be introduced by transfecting the cell with a nucleic acid which encodes the peptide or comprises SEQ ID NO: 1 or a fragment thereof which modulates the expression of a resident Gm2s-1 peptide-encoding gene or transcript.

The invention encompasses a variety of compositions which may be used in the subject methods including modulators of mitotic function, Gm2S-1 peptides, Gm2S-1 peptide-encoding nucleic acids, Gm2S-1 peptide-specific binding agents such as antibodies, and nucleic acid hybridization probes and primers comprising a strand of SEQ ID NO:1 or a fragment thereof sufficient to specifically hybridize with and thereby facilitate identifying, cloning, amplifying and/or modulating the expression of a Gm2S-1 peptide-encoding gene.

DESCRIPTION OF PARTICULAR EMBODIMENTS OF THE INVENTION

The invention provides methods and compositions of selectively disrupting mitotic function in a target cell demonstrating undesirable mitotic function. Hence, the methods may be used to interfere with (e.g. promote, prevent or delay) targeted cell division. The invention is applicable to a wide variety of indications where mitotic function is undesirable quantitatively, qualitatively, spacially, temporally, etc. For example, in one particular embodiment, the methods and compositions are used to control undesirable growth of cells in human neoplasia, such as cancer, restinosis, etc. In another embodiment, the invention is used to prevent the normal division of harmful micororganisms, e.g. pathogenic bacteria such as described in Medical Microbiology $4^{th}$ Ed. (S. Baron, Ed., 1996, UT Med Branch at Galveston). In yet another embodiment, the invention is used to regulate plant seed development by controling the timing of the termination of cell division that allows DNA endoreduplication to occur.

The general methods involve introducing into the target cell an effective amount of a peptide modulator, preferably a disruptor, of mitotic function comprising contiguous acidic amino acids, preferably at least 6, more preferably at least 7, more preferably at least 8 such as Asp or Glu, sufficient to selectively modulate mitotic function of a cell. As demonstrated herein, the invention encompasses a wide variety of suitable methods, amounts, and peptide lengths and compositions, which are readily optimized empirically.

In particular embodiments, the modulator peptide comprises a Gm2S-1 peptide which comprises at least 5, preferably at least 6, more preferably at least 7 of the contiguous acidic amino acids. In other preferred embodiments, the peptide comprise a Gm2S-1 peptide comprising at least an 8, preferably at least a 10, more preferably at least a 20 residue domain of SEQ ID NO:2 sufficient to selectively modulate mitotic function of the cell. Such peptides may derive from the Gm2s-1 signal peptide (residues 01-21 of SEQ ID NO:2), lunasin (residues 22-64 of SEQ ID NO:2), the Gm2S-1 linker peptide (residues 65-81 of SEQ ID NO:2) or alisin (residues SEQ ID NO:2, residues 82-158). In other preferred embodiments, the peptide comprises residues 33-43 of SEQ ID NO:2, residues 85-91 of SEQ ID NO:2, residues 123-127 of SEQ ID NO:2, residues 85-127 of SEQ ID NO:2 and/or at least 12 contiguous residues of SEQ ID NO:2, residues 1-35. The contiguous acidic amino acids are preferably proximate to (i.e. within 12 residues, preferably within 6 residues, more preferably within 3 residues) or at the C-terminus of the modulator. The modulator may comprise a wide variety of additional moieties, especially moities positioned N-terminally relative to the acidic amino acids, including moieties which provide for detection, targeting, stability, proteolytic resistance, etc.

The subject modulators comprising Gm2S-1 peptides provide Gm2S-1 peptide specific activity or function, such as Gm2S-1-specific disruption of mitotic function, ligand/antibody binding or binding inhibitory, immunogenicity, etc. Gm2S-1 peptide-specific activity or function may be determined by convenient in vitro, cell-based, or in vivo assays:

e.g. in vitro binding assays, cell culture assays, in animals (e.g. gene therapy, transgenics, etc.), etc. Binding assays encompass any assay where the molecular interaction of a Gm2S-1 peptide with a binding target is evaluated. The binding target may be a natural intracellular binding target such as a Gm2S-1 peptide regulating protein (e.g. mapmodulin, Ulitzur et al., 1997, PNAS 94, 5084-5089) or other regulator that directly modulates a Gm2S-1 peptide activity or its localization; or non-natural binding target such a specific immune protein such as an antibody, or an Gm2S-1 peptide specific agent such as those identified in bio/chemical screening assays. Gm2S-1 peptide-binding specificity may assayed by mitotic disruption assays described below, binding equilibrium constants (usually at least about $10^7$ $M^{-1}$, preferably at least about $10^8$ $M^{-1}$, more preferably at least about $10^9$ $M^{-1}$), by the ability of the subject peptides to function as negative mutants in a Gm2S-1 peptide-expressing cells, to elicit a Gm2S-1 peptide specific antibody in a heterologous host (e.g. a rodent or rabbit), etc. The Gm2S-1 peptide binding specificity of preferred Gm2S-1 peptides necessarily distinguishes that of the tubulin, MAPs and Mapmodulin.

In particular embodiments, modulators comprising Gm2S-1 peptides are isolated or pure: an "isolated" peptide is unaccompanied by at least some of the material with which it is associated in its natural state, preferably constituting at least about 0.5%, and more preferably at least about 5% by weight of the total peptide in a given sample and a pure peptide constitutes at least about 90%, and preferably at least about 99% by weight of the total peptide in a given sample. The peptides may be synthesized, produced by recombinant technology, or purified from cells. A wide variety of molecular and biochemical methods are available for biochemical synthesis, molecular expression and purification of the subject compositions, see e.g. Molecular Cloning, A Laboratory Manual (Sambrook, et al. Cold Spring Harbor Laboratory), Current Protocols in Molecular Biology (Eds. Ausubel, et al., Greene Publ. Assoc., Wiley-Interscience, New York) or that are otherwise known in the art. Material and methods for the expression of heterologous recombinant peptides in bacterial cells (e.g. *E. coli*), yeast (e.g. *S. Cerevisiae*), animal cells (e.g. CHO, 3T3, BHK, baculovirus-compatible insect cells, etc.). The peptides may be provided uncomplexed with other peptide, complexed in a wide variety of non-covalent associations and binding complexes, complexed covalently with other Gm2S-1 or non-Gm2S-1 peptide sequences (homo or hetero-chimeric peptides), etc.

The invention provides binding agents specific to the claimed modulators, including substrates, agonists, antagonists, natural intracellular binding targets, etc., methods of identifying and making such agents, and their use in diagnosis, therapy and pharmaceutical development. For example, novel peptide-specific binding agents include Gm2S-1 peptide -specific receptors, such as somatically recombined polypeptide receptors like specific antibodies or T-cell antigen receptors (see, e.g Harlow and Lane (1988) Antibodies, A Laboratory Manual, Cold Spring Harbor Laboratory) and other natural intracellular binding agents identified with assays such as one-, two- and three-hybrid screens, non-natural intracellular binding agents identified in screens of chemical libraries, etc. Agents of particular interest modulate Gm2S-1 peptide function, e.g. Gm2S-1 peptide-dependent mitotic disruption.

The invention also provides efficient methods of identifying agents active at the level of a Gm2S-1 modulatable cellular function. Generally, these screening methods involve assaying for compounds which modulate a Gm2S-1 peptide interaction with a natural Gm2S-1 peptide binding target, etc. A wide variety of assays for binding agents are provided including labeled in vitro protein-protein binding assays, immunoassays, cell based assays, etc. The methods are amenable to automated, cost-effective high throughput screening of chemical libraries for lead compounds. Agents that modulate the interactions of a Gm2S-1 peptide with its ligands/natural binding targets can be used to modulate biological processes associated a Gm2S-1 peptide function, e.g. by contacting a cell comprising a Gm2S-1 peptide (e.g. administering to a subject comprising such a cell) with such an agent. Biological processes mediated by Gm2S-1 peptides include a wide variety of cellular events which are mediated when a Gm2S-1 peptide binds a ligand e.g. plant seed growth regulation.

The amino acid sequences of the subject peptides are used to back-translate peptide-encoding nucleic acids optimized for selected expression systems (Holler et al. (1993) Gene 136, 323-328; Martin et al. (1995) Gene 154, 150-166) or used to generate degenerate oligonucleotide primers and probes for use in the isolation of natural Gm2S-1 peptide-encoding nucleic acid sequences ("GCG" software, Genetics Computer Group, Inc, Madison Wis.). Modulator peptide-encoding nucleic acids are used in peptide-expression vectors and incorporated into recombinant host cells, e.g. for expression and screening, e.g. for functional studies such as the efficacy of candidate agents to manipulate modulator peptide-modulated cell function, etc.

The invention also provides Gm2S-1 nucleic acids including hybridization probes and replication/amplification primers having a Gm2S-1 cDNA specific sequence comprising a fragment of a strand of SEQ ID NO:1 sufficient to effect specific hybridization to the complementary strand of SEQ ID NO:1 (i.e. specifically hybridize with a nucleic acid comprising the corresponding opposite strand of SEQ ID NO:1, in the presence of a soybean seed midmaturation library cDNA library). Such primers or probes are at least 12, preferably at least 24, more preferably at least 36 and most preferably at least 96 bases in length. Demonstrating specific hybridization generally requires stringent conditions, i.e. those that (1) employ low ionic strength and high temperature for washing, for example, 0.015 M NaCl/0.0015 M sodium titrate/0.1% SDS at 50° C., or (2) employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C. Another example is use of 50% formamide, 5× SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 (g/ml), 0.1% SDS, and 10% dextran sulfate at 42° C., with washes at 42° C. in 0.2× SSC and 0.1% SDS. Gm2S-1 nucleic acids can also be distinguished using alignment algorithms, such as BLASTX (Altschul et al. (1990) Basic Local Alignment Search Tool, J Mol Biol 215, 403-410). In one embodiment, the subject Gm2S-1nucleic acids comprise Gm2S-1 peptide encoding regions of SEQ ID NO:1; e.g. a Gm2S-1 signal peptide is encoded by bases 17-79, a lunasin peptide by bases 80-208, a lunasin-alisin linker peptide by bases 209-259, an alisin peptide by bases 260-490.

The subject nucleic acids are of synthetic/non-natural sequences and/or are isolated, i.e. unaccompanied by at least some of the material with which it is associated in its natural state, preferably constituting at least about 0.5%, preferably at least about 5% by weight of total nucleic acid present in a given fraction, and usually recombinant, meaning they comprise a non-natural sequence or a natural sequence joined to nucleotide(s) other than that which it is joined to on a natural chromosome. Recombinant nucleic acids comprising the nucleotide sequence of SEQ ID NO:1, or the subject fragments thereof, contain such sequence or fragment at a terminus, immediately flanked by (i.e. contiguous with) a sequence other than that which it is joined to on a natural chromosome, or flanked by a native flanking region fewer than 10 kb, preferably fewer than 2 kb, which is at a terminus or is immediately flanked by a sequence other than that which it is joined to on a natural chromosome. While the nucleic acids are usually RNA or DNA, it is often advantageous to use nucleic acids comprising other bases or nucleotide analogs to provide modified stability, etc.

The subject nucleic acids find a wide variety of applications including use as translatable transcripts, knock-in/out vectors, hybridization probes, PCR primers, diagnostic nucleic acids, etc.; use in detecting the presence of Gm2S-1 genes and gene transcripts and in detecting or amplifying nucleic acids encoding additional Gm2S-1 homologs and structural analogs. In diagnosis, Gm2S-1 hybridization probes find use in identifying wild-type and mutant Gm2S-1 alleles. Gm2S-1 nucleic acids are used to effect and/or modulate cellular expression or intracellular concentration or availability of active Gm2S-1. Methods for effecting the targeted expression of genes encoding the subject modulators are known in the art; see, e.g. Altenschmidt et al., 1997, J Mol Med 75:259-266; Perales et al. 1997, Proc Natl Acad Sci USA 94:6450-6455; Schmidt et al., 1997, Gene 190: 211-216; Oldfield et al., 1993, Human Gene Therapy 4: 39-46; Asgari et al., 1997, Int J. Cancer 71:377-382; He D, et al. 1997, Cancer Res 57:1868-1872. In a particular embodiment, the subject Gm2S-1 peptide is introduced by transfecting the cell with a nucleic acid encoding the peptide particularly, wherein the nucleic acid comprises SEQ ID NO:1 or a fragment thereof. Therapeutic nucleic acid compositions may be advantageously combined and/or used in combination with other therapeutic or prophylactic agents, different from the subject compounds. In many instances, administration in conjunction with the subject compositions enhances the efficacy of such agents, see e.g. *Goodman & Gilman's The Pharmacological Basis of Therapeutics, 9th* Ed., 1996, McGraw-Hill.

Without further description, one of ordinary skill in the art can, using the preceding description and the following illustrative examples, make and utilize the compounds of the present invention and practice the claimed methods. The following working examples therefore, specifically point out preferred embodiments of the present invention, and are not to be construed as limiting in any way the remainder of the disclosure. Other generic configurations will be apparent to one skilled in the art. All publications and patent applications cited in this specification are herein incorporated by reference as if each individual publication or patent application were specifically and individually indicated to be incorporated by reference.

EXAMPLES

Example 1

Cloning of Gm2S-1

In our search for endogenous sulfur-rich proteins in soybean seed to enhance its nutritional quality, we cloned a cotyledon-specific cDNA (Gm2S-1, SEQ ID NO:1) encoding a 2S albumin (4) from Soybean (Glycine max, cv Hodgson 78) from a cDNA library cloned into lambda gt11 using poly-A from midmaturation soybean seed. Briefly, a 500 bp PCR product was obtained using RACE protocol from primers based on 7 internal amino acid (Glu-Glu-Gly-His-Met-Gln-Lys, residues 90-96 of SEQ ID NO:2) of the N-terminus of the purified 8 kDa protein (Revilleza, et al 1996). Template is 2nd stand cDNA derived from mRNA isolated from midmaturation stage soybean seeds. Transcription initiation site was established using cRACE protocol (Maruyama et al, 1995). Clone Gm2S-1has 770 bp of open reading frame which is within a 1.5 kb EcoRI-BamHI near the 3' end of the 2.5 kb cDNA clone that hybridized with the probe. The transcription start site is 17 bp away from the ATG start site. The poly-A signal is 90 bp after the termination codon and the poly-A tail is 138 bp downstream of the poly-A signal.

The complete cDNA codes for a reading frame (SEQ ID NO:2) including a 21 residue signal peptide and a proprotein that is post-translationally processed to yield a 43 amino acid small subunit (lunasin) with a unique carboxyl end containing the cell adhesion motif RGD followed by 8 aspartic acid residues (5), a 17 amino acid linker peptide and a 77 amino acid (8 kDa) large subunit (alisin) rich in sulfur (7.8% methionine) in lysine (13.0%) and cysteine (7.8%). The proprotein is highly hydrophilic with a predicted pI of 5.6. Northern analysis using total RNA from developing soybean embryos (6) showed the Gm2S-1 transcript appearing 3 weeks after flowering, persisting up to 7 weeks after flowering (late maturation) but is completely gone in the mature seed. It is only found in the cotyledon and in no other tissue. Protein is detected using 1-$^{14}$C-iodoacetate method (de Lumen and Kho, 1987) at 4 weeks after flowering and remains in the cotyledon through maturity. This expression coincides with the cell expansion phase of seed development (7).

Example 2

Disrupting Mitotic Function in Bacteria

We sought to produce purified Gm2S-1-derived peptides, including lunasin and alisin peptides, for allergenicity tests using bacterial expression vectors. Initially, PCR amplified fragments that encode lunasin and a lunasin deletion (lunasin-del) mutant (with the 9 aspartic acid deleted from the carboxyl end) were first cloned into pGEM-T (Promega) PCR cloning vector, then cut with EcoR1 and HindIII to release lunasin and lunasin-del gene fragment which were then subcloned into pFLAG-1 bacterial expression vector (Kodak/IBI). Lunasin and lunasin-del pFLAG constructs were used to transform competent DH5 *E. coli* cells using standard heat shock protocol. In the course of these expression experiments, we observed that the basal expression of lunasin in DH5 *E. coli* cells resulted in the formation of elongated and non-septated bacterial filaments. This phenotype was not detected when the genes encoding the large subunit peptide and lunasin with a deleted poly-aspartyl end (lunasin-del) were expressed in DH5 cells, indicating that the carboxyl end of lunasin is necessary for disrupting mitotic function in bacterial cell division.

Similar mitotic disruption is observed using a large panel of lunasin and alisin deletion mutant peptides (lunasin-del-n and alisin-del-n) and lunasin/alisin-like synthetic peptides (Gm2S-1-syn-n). Exemplary active lunasin-del peptides in these bacterial studies include (using N →C nomenclature convention):

lunasin-del-1: MRG—residues 57-64 of SEQ ID NO:2 fusion protein
lunasin-del-2: OmpA—residues 54-64 of SEQ ID NO :2 fusion protein
lunasin-del-3: lacZ α-fragment—residues 48-63 of SEQ ID NO:2 fusion protein
lunasin-del-4: FtsZ—residues 26-64 of SEQ ID NO:2 fusion protein
lunasin-del-5: lacI—residues 57-64 of SEQ ID NO:2 fusion protein
lunasin-del-6: lacZ α-fragment—residues 54-64 of SEQ ID NO:2 fusion protein
lunasin-del-7: OmpA—residues 44-63 of SEQ ID NO:2 fusion protein
lunasin-del-8: FLAGG—residues 30-64 of SEQ ID NO:2 fusion protein
lunasin-del-9: lacZ α-fragment—residues 57-64 of SEQ ID NO:2 fusion protein
lunasin-del-10: FtsZ—residues 54-64 of SEQ ID NO:2 fusion protein
lunasin-del-11: Met-Glu-Lys-Ile-Gln-Gly-Arg-Gly (SEQ ID NO:3)—residues 40-63 of SEQ ID NO:2 fusion protein
lunasin-del-12: Met-Glu-Lys-Ile-Gln-Gly-Arg-Gly (SEQ ID NO:3)—residues 34-64 of SEQ ID NO:2 fusion protein.

Exemplary active alisin-del peptides in these bacterial studies include:
alisin-del-1: MRG—residues 84-91 of SEQ ID NO:2 fusion protein
alisin-del-2: OmpA—residues 82-92 of SEQ ID NO:2 fusion protein
alisin-del-3: lacZ α-fragment—residues 123-130 of SEQ ID NO:2 fusion protein
alisin-del-4: FtsZ—residues 120-132 of SEQ ID NO:2 fusion protein
alisin-del-5: lacI—residues 84-91 of SEQ ID NO:2 fusion protein
alisin-del-6: lacZ α-fragment—residues 82-92 of SEQ ID NO:2 fusion protein
alisin-del-7: OmpA—residues 123-130 of SEQ ID NO:2 fusion protein
alisin-del-8: FLAGG—residues 120-132 of SEQ ID NO:2 fusion protein
alisin-del-9: lacZ α-fragment—residues 84-91 of SEQ ID NO:2 fusion protein
alisin-del-10: FtsZ—residues 82-92 of SEQ ID NO:2 fusion protein
alisin-del-11: Met-Glu-Lys-Ile-Gln-Gly-Arg-Gly (SEQ ID NO:3)—residues 123-130 of SEQ ID NO:2 fusion protein
alisin-del-12: Met-Glu-Lys-Ile-Gln-Gly-Arg-Gly (SEQ ID NO:3)—residues 120-132 of SEQ ID NO:2 fusion protein.

Exemplary active Gm2S-1-syn peptides in these bacterial studies include:
Gm2S-1-syn-1: MRG—octa-aspartate fusion protein
Gm2S-1-syn-2: OmpA—tetra-aspartate-tetra-glutamate fusion protein
Gm2S-1-syn-3: lacZ α-fragment—nona-aspartate fusion protein
Gm2S-1-syn-4: FtsZ—deca-aspartate fusion protein
Gm2S-1-syn-5: lacI—octa-glutamate fusion protein
Gm2S-1-syn-6: lacZ α-fragment—nona-glutamate fusion protein
Gm2S-1-syn-7: OmpA—deca-glutamate fusion protein
Gm2S-1-syn-8: FLAGG—tetra(aspartate-glutamate) fusion protein
Gm2S-1-syn-9: lacZ α-fragment—tri(aspartate-glutamate-aspartate) fusion protein
Gm2S-1-syn-10: FtsZ—deca-(glutamate-aspartate) fusion protein
Gm2S-1-syn-11: Met-Glu-Lys-Ile-Gln-Gly-Arg-Gly-tetra-glutamate-tetra aspartate fusion protein
Gm2S-1-syn-12: Met-Glu-Lys-Ile-Gln-Gly-Arg-Gly-tetra (glutamate-aspartate-glutamate) fusion protein
Gm2S-1-syn-13: MRG—tri-glutamate-penta aspartate fusion protein.

The peptides demonstrate mitotic disruption with several alternative methods of introduction, including direct medium uptake, uptake facilitated by chaotropic agents including detergents (e.g. TWEEN20, etc.), guanadine salts, etc., pulsed electric field, liposome fusion, etc. Alternatively, the peptides are introduced indirectly by expression within the targeted microbe. Such expression may be effected by transiently or by upregulation of a stably introduced peptide-encoding gene. A wide variety of well-established methods are known in the art for facilitating introduction, expression and/or stable integration of exogenous genes in microbial hosts.

Activity is shown in a wide variety of other tested bacteria, particularly pathogenic bacteria. Exemplary bacteria demonstrating mitotic disruption with peptides including the foregoing lunasin-del, alisin-del and Gm2S-1-syn peptides. Such bacteria include:
1: ATCC No:6357: *Chromobacterium violaceum*
2: ATCC No:25419: *Serratia marcescens* Bizi
3: ATCC No:19107: *Vibrio* sp. Depositors/D
4: ATCC No:55191: *Streptococcus agalactiae*
5: ATCC No:55192: *Streptococcus agalactiae*
6: ATCC No:55193: *Streptococcus agalactiae*
7: ATCC No:19106: *Vibrio tubiashii* Hada
8: ATCC No:19105: *Vibrio tubiashii* Hada
9: ATCC No:19108: *Vibrio alginolyticus*
10: ATCC No:55194: *Streptococcus agalactiae*
11: ATCC No:700024: *Vibrio ichthyoenteri*
12: ATCC No:32751: *Fusarium* sp. Depositors
13: ATCC No:700023: *Vibrio ichthyoenteri*
14: ATCC No:19109: *Vibrio tubiashii* Hada et
15: ATCC No:19310: *Pseudomonas syringae* sub
16: ATCC No:15302: *Mycoplasma gallisepticum*
17: ATCC No:15310: *Burkholderia mallei*
18: ATCC No:43115: *Spiroplasma phoeniceum* S
19: ATCC No:24458: *Metarhizium anisopliae*
20: ATCC No:62337: *Cladosporium tenuissimum*

Example 3

Disrupting Mitotic Function in Plants Seeds

In this example, we show that the genes coding Gm2S-1 peptides can de-arrest cell division when over-expressed or induced in storage parenchyma cells of the cotyledon. In particular experiments, lunasin peptides demonstrate mitotic disruption in cotyledon and endosperm parynchematous cells using other binary vectors for *Agrobacterium*-mediated transformation (pPZP family of binary vectors and pBIN19) and other cloning vectors for biolistic method of plant transformation (i.e. pBluescript series of cloning vectors and pUC family of cloning vectors).

Cereal endosperm and legume cotyledon make up at least 85% of the seed weight and that seed size is genetically correlated to crop yield by at least 80%. Hence, in vivo manipulation of lunasin gene expression provided us an effective means of increasing the yield of major seed crops. Specifically, by altering the temporal and spatial pattern of lunasin expression in parynchematous cells in developing seeds, we are able to significantly increase the length and magnitude of the cell expansion phase and the number of cells that undergo DNA endoreduplication, resulting in larger than normal seeds. To accomplish this, the 5' regulatory regions of soybean conglycinin gene (a 170 bp DNA sequence element that is 200 nucleotides upstream of the transcription start site conferring cotyledon-specific expression (Chen et al., 1988, EMBO J 7:297) and rice glutelin gene (a 121 bp DNA sequence element that is 437/317 nucleotide upstream of the transcription start site conferring endosperm-specific expression (Yoshihara and Takaiwa, 1996, Plant Cell Physiol 37:107) are inserted into the −90 position of the CaMV 35S promoter which are then fused to the DNA fragments encoding the in-frame translation of lunasin and lunasin-del peptides. The DNA constructs are ligated to the binary vector, pKYLX71 (Lloyd et al., 1992, Science 258:1773) for *Agrobacterium* transformation and to pGEM-3Zf(+) vector (Promega) for biolistic transformation (Cho et al., 1995, Plant Mol Biol Rept 13:255). *Agrobacterium*-mediated transformation using the cotyledon-specific DNA constructs is utilized for most dicots, i.e. legumes (soybean, peas, peanuts and kidney beans), *Arabidopsis thaliana* and tobacco. For monocots like the cereal grain crops, wheat, rice, barley, rye and corn, the biolistic method of transformation is utilized using the endosperm-specific DNA constructs. The expression of the lunasin peptide in the developing seeds of all these plant species are monitored by immunolocalization using antibodies derived specifically to the carboxyl end epitope of the lunasin peptide. The overexpression of lunasin in a larger proportion of parynchematous cells leads to mitotic cell cycle arrest and allows the cells to undergo extra cycles of DNA endoreduplication that leads to larger cells and consequently larger seed sizes.

Similar mitotic disruption is observed using a large panel of lunasin and alisin deletion mutant peptides (lunasin-del-n and alisin-del-n) and lunasin/alisin-like synthetic peptides (Gm2S-1-syn-n). Exemplary active lunasin-del peptides in these plant transformation studies include:

lunasin-del-1: MRG—residues 57-64 of SEQ ID NO:2 fusion protein
lunasin-del-2: α-tubulin—residues 54-64 of SEQ ID NO:2 fusion protein
lunasin-del-3: β-tubulin—residues 48-63 of SEQ ID NO:2 fusion protein
lunasin-del-4: MAP2 —residues 26-64 of SEQ ID NO:2 fusion protein
lunasin-del-5: Mapmodulin—residues 57-64 of SEQ ID NO:2 fusion protein
lunasin-del-6: GFP—residues 54-64 of SEQ ID NO:2 fusion protein
lunasin-del-7: MAP4—residues 44-63 of SEQ ID NO:2 fusion protein
lunasin-del-8: FLAGG—residues 30-64 of SEQ ID NO:2 fusion protein
lunasin-del-9: α-tubulin—residues 57-64 of SEQ ID NO:2 fusion protein
lunasin-del-10: β-tubulin—residues 54-64 of SEQ ID NO:2 fusion protein
lunasin-del-11: SEQ ID NO:2, res. 48-55—res. 40-63 of SEQ ID NO:2 fusion protein
lunasin-del-12: SEQ ID NO:2, res. 48-55—res. 34-64 of SEQ ID NO:2 fusion protein
lunasin-del-13: MRG-octa-aspartate fusion protein
lunasin-del-14: SEQ ID NO:2, residues 48-55—octa-aspartate fusion protein
lunasin-del-15: SEQ ID NO:2, residues 48-55—MRG-octa-aspartate fusion protein
lunasin-del-16: SEQ ID NO:2, residues 48-55—SEQ ID NO:2, residues 48-55—octa-aspartate fusion protein
lunasin-del-17: MRG-tetrta-aspartate-tetra glutamate fusion protein
lunasin-del-18: SEQ ID NO:2, residues 48-55—octa-glutamate fusion protein
lunasin-del-19: SEQ ID NO:2, residues 1-21—MRG-deca-glutamate fusion protein
lunasin-del-20: SEQ ID NO:2, residues 48-55—SEQ ID NO:2, residues 48-55-tetra-aspartate-tetra glutamate fusion protein Exemplary active alisin-del peptides in these plant studies include:

alisin-del-1: MRG—residues 84-91 of SEQ ID NO:2 fusion protein
alisin-del-2: α-tubulin—residues 82-92 of SEQ ID NO:2 fusion protein
alisin-del-3: β-tubulin—residues 123-130 of SEQ ID NO:2 fusion protein
alisin-del-4: FLAGG—residues 120-132 of SEQ ID NO:2 fusion protein
alisin-del-5: GFP—residues 84-91 of SEQ ID NO:2 fusion protein
alisin-del-6: mapmodulin—residues 82-92 of SEQ ID NO:2 fusion protein
alisin-del-7: MAP2 —residues 123-130 of SEQ ID NO:2 fusion protein
alisin-del-8: MAP4 —residues 120-132 of SEQ ID NO:2 fusion protein
alisin-del-9: α-tubulin—residues 84-91 of SEQ ID NO:2 fusion protein
alisin-del-10: β-tubulin—residues 82-92 of SEQ ID NO:2 fusion protein
alisin-del-11: SEQ ID NO:2, res. 48-55—res. 123-130 of SEQ ID NO:2 fusion protein
alisin-del-12: SEQ ID NO:2, res. 48-55—res. 120-132 of SEQ ID NO:2 fusion protein Exemplary active Gm2S-1-syn peptides in these plant studies include:

Gm2S-1-syn-1: MRG—octa-aspartate fusion protein
Gm2S-1-syn-2: α-tubulin—tetra-aspartate-tetra-glutamate fusion protein
Gm2S-1-syn-3: β-tubulin—nona-aspartate fusion protein
Gm2S-1-syn-4: FLAGG—deca-aspartate fusion protein
Gm2S-1-syn-5: GFP—octa-glutamate fusion protein
Gm2S-1-syn-6: MAP2—nona-glutamate fusion protein
Gm2S-1-syn-7: Mapmodulin—deca-glutamate fusion protein
Gm2S-1-syn-8: FLAGG—tetra(aspartate-glutamate) fusion protein
Gm2S-1-syn-9: GFP—tri(aspartate-glutamate-aspartate) fusion protein
Gm2S-1-syn-10: MAP2—deca-(glutamate-aspartate) fusion protein
Gm2S-1-syn-11: α-tubulin—tetra-glutamate-tetra aspartate fusion protein
Gm2S-1-syn-12: β-tubulin—tetra (glutamate-aspartate-glutamate) fusion protein
Gm2S-1-syn-13: MAP4—tri-glutamate-penta aspartate fusion protein The peptides demonstrate mitotic disruption when upregulated in transgenic plants that were transformed by fusing the coding regions with 5' promoter regions from cotyledon and endosperm-specific genes including cotyledon-specific genes such as At2S1, At2S2 and Gm2S-1; and endosperm-specific genes such as Hth-1, prolamine, glutenin-1D1, beta-glucosidase, globulin-1, zein (pML1), etc.

Example 4

Disrupting Mitotic Function in Mammalian Cells

The filamentation without septation phenotype in prokaryotes is caused by mutations that disrupt Fts-Z (protofilament) polymerization in the bacterial cell division plate (9). Fts-Z is hypothesized to be the evolutionary precursor of eukaryotic tubulins since they are structurally similar and both play important roles in cell division (9). The disruption of Fts-Z-mediated bacterial cell division caused by Gm2S-1 peptides and their activity in plant cells led us to hypothesize that this soybean peptide could have a similar effect in eukaryotic cell division generally, including mammalian and human cells, particularly transformed or cancer cells.

To initially prove this hypothesis, cultured murine hepatoma cells (Hepa 1c1c7) were transiently transfected with a mammalian expression vector, pEGFP-C1 (10), that contains the lunasin gene and lunasin-del mutant (minus the 9 aspartic acid residues) tagged with the gene for green fluorescent protein (GFP) at its amino end. By tagging with GFP, we were able to monitor transfected cells and observe cellular changes by fluorescence microscopy and to carry out cell cycle analysis by flow cytometry. These data show the effect of lunasin and lunasin-del expression in actively dividing murine hepatoma cells. Normal cell division occurred in cells transfected with lunasin-del at 24 h, 48 h and 72 h post-transfection. No morphological changes were observed in transfected and untransfected cells as shown by phase contrast and GFP fluorescence. At 72 h, at least 3 cycles of cell division resulted in the dilution of GFP fluorescence in these cells as a result of the transient expression of lunasin-del.

In contrast to the normal cell division observed in the deletion mutant control, the expression of lunasin in murine hepatoma cells resulted in gross morphological changes as shown in phase contrast and fluorescent images after 48 h, 72 h and 80 h. At 48 h, the cells were larger and showed generally brighter GFP fluorescence compared to lunasin-del-transfected cells. By staining with low concentration of propidium iodide (10), condensed metaphase chromosomes were visualized by phase contrast microscopy and exhibited dispersed orientation instead of normal alignment along a metaphase plate. At 72 h, lunasin-transfected cells had lysed, showing cell membrane degradation and the expulsion of condensed chromosomes from the burst cell. GFP fluorescence was associated with the chromosomal fragments indicating attachment of lunasin to the chromosomes even after the disintegration of the cellular membrane. Further fragmentation of the chromosomes and consequent dilution of GFP fluorescence were observed at 80 h after transfection.

The abnormal orientation of metaphase chromosomes, the enlarged cell morphology and the non-dilution of GFP in lunasin-transfected cells after 48 h, suggest the occurrence of mitotic arrest. To determine whether there is an increase in the proportion of murine hepatoma cells at the mitotic stage in lunasin-transfected cells, flow cytometry and cell cycle analysis were done on 12 independent transfections using pEGFP-C1 constructs of lunasin and lunasin-del, and the pEGFP-C1 vector alone (11). By varying electroporation parameters and using different cell densities in each transfection experiment, efficiencies ranging from 0.3 to 15% were obtained (11). The proportion of cells undergoing G2/M phase was measured after 48 h. For each transfection experiment, the lunasin-transfected cells had a consistently higher proportion of cells at G2/M compared to the two controls, lunasin-del and pEGFP-N1-transfected cells, as indicated by the positive values for G2/M arrest. G2/M arrest was calculated as the difference between the proportion of G2/M cells in the lunasin-transfected cells and the average of the two controls, whose G2/M percentile values were not statistically different from each other (11). To determine whether there is any relationship between G2/M arrest and lunasin transfection efficiency, a linear regression graph was generated and the Pearson product moment correlation was computed using the two variables. There was a significant positive correlation between mitotic arrest and transfection efficiency of the lunasin gene, indicating that the expression of lunasin resulted in mitotic arrest of dividing murine hepatoma cells. Thus, it is possible to increase the proportion of cells that get arrested at mitosis, by improving the transfection efficiency of the lunasin gene into actively dividing cells.

Unlike most anti-mitotic drugs that attenuate cell division (12), the transient expression of lunasin not only led to mitotic arrest but also to cell lysis and the break up of condensed chromosomes within a short period of time. DNA fragmentation, a hallmark of late apoptotic response, was consequently measured using the TUNEL assay (13) in lunasin and lunasin-del-transfected cells at 24 h, 48 h and 72 h post-transfection. The lunasin-del-transfected cells showed no apoptotic response at 24 h and 48 h after transfection. On the other hand, some of the lunasin-transfected cells were apoptotic (yellow fluorescence) as early as 24 h after transfection. The apoptotic cells exhibited deformed cell morphology and non-adherence to the glass surface at 48 h. At 72 h, the condensed chromosomes visualized by phase contrast started to get disjointed and fragmented as shown by the TUNEL test. Upon cell lysis, the chromosomes further broke up into smaller DNA fragments as revealed by phase contrast and by the TUNEL assay.

The mitotic arrest caused by lunasin expression appeared to occur at the metaphase-anaphase stage and might involve changes in spindle fiber assembly as a result of the disruption of microtubule dynamics which is the common mechanism among antimitotic agents (12). To determine whether the same mechanism is involved in the antimitotic effect of lunasin, microtubule formation was visualized by indirect immunofluorescent labeling of tubulin in lunasin and lunasin-del-transfected murine hepatoma cells (14). There was normal spindle fiber assembly at anaphase in actively dividing cells transfected with lunasin-del. In contrast, the lunasin-transfected cells after 48 h showed abnormal elongation of spindle fibers emanating from the two opposite spindle poles. The normal fusiform shape of spindle fiber assembly during metaphase and early anaphase did not form in the mitosis-arrested cells, instead, the spindle fibers projected out of the opposite centrioles in a misaligned orientation. At 72 h after transfection, the elongated spindle fibers were still intact and appear to span the length of the abnormally large cell although the midsection of the cell had already started to lyse. To visualize the chromosomal DNA in these lysing cells, propidium iodide was added to the immunofluorescence labeling reaction (14). A lunasin-transfected cell that had been arrested at metaphase stage revealed that the chromosomal mass was assymetrically located near one centriole but with some chromosomes appearing to migrate to the opposite pole and to leak out of the lysing cell.

The abnormal spindle fiber morphology and the aberrant chromosome movement during mitosis that eventually led to apoptosis suggest two models of mitotic arrest in lunasin-transfected cells based on the effect of lunasin on microtubule dynamics and its association to chromosomal DNA. The loss of antimitotic and cytotoxic effect upon deletion of the negatively charged poly-aspartic acid carboxyl end indicates that the antimitotic effect of lunasin involves electrostatic interactions with the cell division machinery.

The mechanism of mitotic arrest by antimitotic drugs like vinblastine, colchicine, nocodazole and taxol involves the binding of these compounds to the plus ends of the microtubule leading to the disruption of spindle microtubule dynamics (12). Vinblastine, colchicine and nocodazole depolymerize microtubules at high concentrations while taxol promotes polymerization and inhibits microtubule disassembly thus blocking spindle function during mitosis (12). Unlike these compounds however, lunasin with its highly acidic carboxyl end does not appear to bind directly to microtubules (i.e. via the acidic C-terminal region of tubulin) but could affect microtubule dynamics indirectly through its association with microtubule-associated proteins (MAPs). In vitro experiments on rat brain microtubules showed that large molecular weight synthetic acidic amino acid polymers can bind to the basic, tubulin-binding region of MAPs via electrostatic interaction (15). Nonneuronal mammalian cell MAPs include the mitotic motors, dynein and kinesin (16) as well as MAP4 that promote microtubule assembly and stability in vitro (17) although its removal from microtubules in vivo did not produce any cellular changes during mitosis (18). However, the possible inhibition of dynein and kinesin binding to microtubules (16) by the competitive coupling of the negatively-charged lunasin to the positively-charged microtubule binding site of these motor proteins could account for the aberrant movement and assymetric distribution of chromosomes during mitosis in the lunasin-transfected cells.

It is apparent from GFP fluorescence images after cell lysis that lunasin was still bound to the fragmenting chromosomes, most probably through the formation of complexes with the highly basic histone proteins that make up chromatin. In this model of mitotic arrest, the formation of lunasin-chromatin-DNA complex at prometaphase prevents the attachment of the plus end of microtubules to the chromosomes, particularly in the heterochromatized region of the kinetochore thus inhibiting the congression of the chromosomes to the metaphase plate. The misaligned spindle orientation could also be indicative of the inability of the spindle fibers to form bipolar attachment to the kinetochore thereby preventing the formation of spindle tension (19) and consequently of the normal fusiform shape of spindle fiber assembly at metaphase (20). The observed elongated spindle fibers could also be the consequence of the non-attachment of spindle microtubules to the kinetochore. This could result from the continued microtubule polymerization and the inhibition of microtubule disassembly, caused by the disruption of the normal dynamics of kinetochore microtubules during mitosis (20, 21).

The nature of cell division disruption by lunasin expression in murine hepatoma cells suggests that its effect should not be specific to a particular cell type. To test whether the same anti-mitotic effect occurs in other actively dividing cells, lunasin and lunasin-del pEGFP-C1 constructs were transfected into human breast cancer cells (MCF-7) (22) and the TUNEL assay was conducted to detect apoptosis (13). MCF-7 cells transfected with lunasin-del did not show any aberrant cell division nor apoptosis at 48 h after transfection. In contrast, DNA fragmentation and abnormal chromosomal movement at mitosis were observed in the lunasin-transfected cells at 48 h post-transfection. Like in murine hepatoma cells, lunasin expression in human breast cancer cells also resulted in cell lysis, chromosomal fragmentation and apoptosis. The apoptotic response associated with the antimitotic effect of lunasin in murine hepatoma and human breast cancer cells is similar to the unusually rapid response of T47D (human breast cancer cell line) to taxol and nocodazole and the sensitivity of this cell line to the mitotic spindle inhibitors has been attributed to the reduced levels of the human mitotic checkpoint protein, hsMAD2, in the kinetochore (23)

Similar mitotic disruption is observed using a large panel of lunasin and alisin deletion mutant peptides (lunasin-del-n and alisin-del-n) and lunasin/alisin-like synthetic peptides (Gm2S-1-syn-n). Exemplary active lunasin-del peptides in these mammalian studies include (again using N→C nomenclature convention):

lunasin-del-1: MRG—residues 57-64 of SEQ ID NO:2 fusion protein
lunasin-del-2: α-tubulin—residues 54-64 of SEQ ID NO:2 fusion protein
lunasin-del-3: β-tubulin—residues 48-63 of SEQ ID NO:2 fusion protein
lunasin-del-4: MAP2 —residues 26-64 of SEQ ID NO:2 fusion protein
lunasin-del-5: Mapmodulin—residues 57-64 of SEQ ID NO:2 fusion protein
lunasin-del-6: GFP—residues 54-64 of SEQ ID NO:2 fusion protein
lunasin-del-7: MAP4—residues 44-63 of SEQ ID NO:2 fusion protein
lunasin-del-8: FLAGG—residues 30-64 of SEQ ID NO:2 fusion protein
lunasin-del-9: CYCLIN A—residues 57-64 of SEQ ID NO:2 fusion protein
lunasin-del-10: CYCLIN B1—residues 54-64 of SEQ ID NO:2 fusion protein
lunasin-del-11: CYCLIN B2—residues 40-63 of SEQ ID NO:2 fusion protein
lunasin-del-12: CYCLIN B3—residues 34-64 of SEQ ID NO:2 fusion protein
lunasin-del-13: SH2—octa-aspartate fusion protein
lunasin-del-14: SH3—octa-aspartate fusion protein
lunasin-del-15: SEQ ID NO:2, residues 48-55—MRG-octa-aspartate fusion protein
lunasin-del-16: SEQ ID NO:2, residues 48-55—SEQ ID NO:2, residues 48-55—octa-aspartate fusion protein
lunasin-del-17: MRG-tetrta-aspartate-tetra glutamate fusion protein
lunasin-del-18: SEQ ID NO:2, residues 48-55-octa-glutamate fusion protein
lunasin-del-19: SEQ ID NO:2, residues 1-21-MRG-deca-glutamate fusion protein
lunasin-del-20: SEQ ID NO:2, residues 48-55—SEQ ID NO:2, residues 48-55—tetra-aspartate-tetra glutamate fusion protein Exemplary active alisin-del peptides in these mammalian studies include:
alisin-del-1:MRG—residues 84-91 of SEQ ID NO:2 fusion protein
alisin-del-2: α-tubulin—residues 82-92 of SEQ ID NO:2 fusion protein
alisin-del-3: β-tubulin—residues 123-130 of SEQ ID NO:2 fusion protein
alisin-del-4: FLAGG—residues 120-132 of SEQ ID NO:2 fusion protein
alisin-del-5: GFP—residues 84-91 of SEQ ID NO:2 fusion protein alisin-del-6: mapmodulin—residues 82-92 of SEQ ID NO:2 fusion protein
alisin-del-7: MAP2-residues 123-130 of SEQ ID NO:2 fusion protein
alisin-del-8: MAP4-residues 120-132 of SEQ ID NO:2 fusion protein
alisin-del-9: CYCLIN A—residues 84-91 of SEQ ID NO:2 fusion protein
alisin-del-10: CYCLIN B1—residues 82-92 of SEQ ID NO:2 fusion protein
alisin-del-11: CYCLIN B2—residues 123-130 of SEQ ID NO:2 fusion protein
alisin-del-12: CYCLIN B3—residues 120-132 of SEQ ID NO:2 fusion protein
alisin-del-13: SH2—residues 84-91 of SEQ ID NO:2 fusion protein
alisin-del-14: SH3—residues 82-92 of SEQ ID NO:2 fusion protein Exemplary active Gm2S-1-syn peptides in these mammalian studies include:
Gm2S-1-syn-1: MRG—octa-aspartate fusion protein
Gm2S-1-syn-2: α-tubulin—tetra-aspartate—tetra-glutamate fusion protein
Gm2S-1-syn-3: β-tubulin—nona-aspartate fusion protein Gm2S-1-syn-4: FLAGG—deca-aspartate fusion protein Gm2S-1-syn-5: GFP—octa-glutamate fusion protein Gm2S-1-syn-6: MAP2—nona-glutamate fusion protein Gm2S-1-syn-7: Mapmodulin—deca-glutamate fusion protein Gm2S-1-syn-8: CYCLIN A—tetra(aspartate-glutamate) fusion protein Gm2S-1-syn-9: CYCLIN B1—tri(aspartate-glutamate-aspartate) fusion protein Gm2S-1-syn-10: CYCLIN B2—deca-(glutamate-aspartate) fusion protein Gm2S-1-syn-11: CYCLIN B3—tetra-glutamate—tetra aspartate fusion protein Gm2S-1-syn-12: SH2—tetra (glutamate-aspartate-glutamate) fusion protein Gm2S-1-syn-13: SH3—tri-glutamate—penta aspartate fusion protein The peptides demonstrate mitotic disruption with several alternative methods of introduction, including direct medium uptake, uptake facilitated by chaotropic agents including detergents (e.g. TWEEN20, etc.), gaunadine salts, etc., pulsed electric field, liposome fusion, etc. Alternatively, the peptides are introduced indirectly by expression within the targeted cell. Such expression may be effected by transciently or by upregulation of a stably introduced peptide-encoding gene.

Activity is shown in a wide variety of other tested cells, particularly pathogenic cell-types. Exemplary cells demonstrating mitotic disruption with peptides including lunasin-del and lunasin-syn-1-12 include: transformed mammalian cells including: ATCC Nos: CRL-1435: PC-3; HTB-81: DU 145; HB-11430: 9H10-A4; HB-9119: P25.48; HB-9120: P25.91; CRL-2220: CA-HPV-10; HB-9140: P25.15; CRL-1740: LNCaP clone; CRL-10995: LNCaP-FGC; HB-8279: T16; CRL-7535: Hs 804.Sk; CRL-2221: PZ-HPV-7; CRL-5813: NCI-H660; CRL-2222: YPEN-1; HB-8428: S27; HB-10494: 7E11C5; HB-8051: F5-A-1/22.8.13; HB-8525: RLSD09; HB-8527: RLSD06 and CRL-7930: IK-15; myeloma cells including ATCC Nos: TIB-98: RDP 45/20; TIB-157: LS 136; HB-88: Bet-2; HB-43: 1410 KG7; HB-45: 141PF11; HB-100: Bet-1; HB-121: E5BB3IIA2; TIB-132: 80 V 5B4 CRL-1869: 6F4C5; TIB-17: XS63;HB-128: 2E.6; HB-9762: NUH-2; TIB-194: 2F.11.15; TIB-109: N-S.8.1; HB-8478: C-2; HB-8479: LA-5; HB-8480: LA-4; HB-8481: Re-2; HB-8482: Re-1; HB-8705: L21-6; hepatic carcinoma including ATCC Nos: CRL-7549: Hs 817.T ; HB-8065: Hep G2; CRL-7930: IK-15; CRL-7929: IK-6; CRL-7454: Hs 715.K; CRL-6504: VX7; CRL-7721: MB 157;HB-8431: ME195; HB-8411: MF116;CRL-7369: Hs 607.T ; CRL-7758: TE 206.T; CRL-7192: Hs 227.T; HB-8410: MF61; CRL-7335: Hs 566(A).T; CRL-7211: Hs 249.T; CRL-7214: Hs 257.T; CRL-7833: Hs 172.T; CRL-7870: Hs 740.T; CRL-7139: Hs 187.T; CRL-7159: Hs 200.T; colon carcinoma cells including ATCC Nos: CRL-7214: Hs 257.T; CRL-7168: Hs 207.T; CRL-7892: Hs 844.T; CRL-7423: Hs 682.T; CRL-7884: Hs 785.T; CRL-7351: Hs 586.T; CRL-7139: Hs 187.T; -7159: Hs 200.T; CRL-7202: Hs 237.T; CRL-7399: Hs 674.T/cc; CRL-7184: Hs 219.T; CRL-7213: Hs 255.T; CRL-7207: Hs 241.T; CRL-7172: Hs 210.T; CRL-7352: Hs 587.Int; CRL-7376: Hs 614.T; CRL-7179: Hs 217.T; CRL-7456: Hs 722.T; CRL-7435: Hs 698.T; CCL-220: COLO 320DM; carcinoma cells including ATTC Nos: CRL-7439: Hs 700.Sk; CCL-200: CCD-13Lu; CRL-1677: IA-XsSBR; HB-8779: AS 33; CRL-1837: SU.86.86; HB-8059: 1116-NS-19-9; CRL-1687: BxPC-3; HB-11028: 100-310; CRL-2133: DSL-6B/C1; CRL-2172: SW 1990; CRL-2132: DSL-6A/C1; HTB-134: Hs 766T; HTB-80: Capan-2; CRL-2141: TGP47; CRL-2136: TGP49; CRL-1997: HPAF-II; HTB-79: Capan-1; CRL-1674: ARIP; CRL-1918: CFPAC-1; CCL-91:BF-2; leukemia cells including ATTC Nos: CRL-8012: FL74-UCD-1; TIB-57: T27A; TIB-58: D2N; TIB-55: BB88; TIB-56: DIB; CRL-6070: R2LBLN; CRL-6047: 2LBLN; CRL-6048: 3LBLN; CRL-6049: 5LBLN; CRL-6050: 6LBLN; CRL-6045: 2FLB.Ln n; TIB-192: M1; CRL-6039: FB3.Thy; CRL-6046: LBLN; CRL-6038: FB3.Ln; TIB-59: BC16A; TIB-60: BC3A; CRL-10423: JM1; CRL-6359: JLS-V5; CRL-7739: TE 90.Sk; osteosarcoma cells including ATTC Nos: CRL-7134: Hs 184.T; CRL-6114: FC95.Thy; CRL-7780: TO 203.T; CRL-7943: T1-73; CRL-7783: HT 728.T; CRL-7722: Murphy; CRL-7765: TE 417.T; CRL-7135: Hs 185.T; CRL-7628: Hs 890.T;CRL-7764: TE 415.T; CRL-7766: TE 418.T; CRL-7626: Hs 889.T; CRL-7606: Hs 870.T; CRL-7922: F1-73; CRL-7520: Hs 792(A); CRL-7010: Hs 13.T; CRL-7823: Hs 14.T; CRL-7521: Hs 792(B); CRL-7140: Hs 188.T; CRL-7263: Hs 387.T; melanoma cells including ATTC Nos: CRL-1676: WM-266-4; CRL-1585: C32; CRL-1424: G-361; HB-8672: WI-MN-1; CRL-7360: Hs 600.T; HB-9348: NR-ML-06; CRL-7357: Hs 597.T; CRL-7637: Hs 895.T; CRL-1675: WM-1 15; CRL-7299: Hs 432.T; CRL-9607: HMCB; CCL-53.1: Clone M-3; CRL-7568: Hs 834.T; CRL-7687: Hs 936.T; CRL-7572: Hs 839.T; CRL-1980: COLO 829BL; CRL-7597: Hs 862.T; CRL-7375: Hs 613.Sk; CRL-7686: Hs 936.T; HB-9349: NR-ML-03; retinoblastoma cells including ATTC Nos: HTB-18: Y79; TIB-198: PI 153/3; HTB-169: WERI-Rb-1; CCL-2: HeLa; HTB-31: C-33 A; CCL-2.3; CRL2207: PA317LXSN6E7; CRL2205:PA317LXSN16E7; CRL-5804: NCI-H187; HTB-32: HT-3; CRL-581 1: NCI-H526; CRL-5809: NCI-N417; cancer human breast cells including ATTC Nos: HB-10807: 741F8-2B9; HB-10811: 452F2-1B2; CRL-7034: Hs 54.T; HB-8630: Hybridoma 23; CRL-7789: HT 762.T; CRL-7369: Hs 607.T; CRL-7853: Hs 631.T; CRL-7940: SW527; CRL-7335: Hs 566(A); CRL-7368: Hs 606; CRL-7145: Hs 190.T; CRL-7277: Hs 402.T; CRL-7365: Hs 605.T; CRL-7484: Hs 743.T; CRL-7574: Hs 841.T; CRL-7584: Hs 851.T; CRL-7596: Hs 861.T; CRL-7208: Hs 243.T; CRL-7212: Hs 252.T; CRL-7236: Hs 319.T; skin cancer cells including ATTC Nos: CRL-7360: Hs 600.T; CRL-7779: TO 175.T; CRL-7357: Hs 597.T; CRL-7043: Hs 63.T; CRL- 7299: Hs 432.T; CRL-7233: Hs 295.T; CRL-7590: Hs 854.T; CRL-7572: Hs 839.T; CRL-7314: Hs 523.Sk; CRL-7597: Hs 862.T; CRL-7781: HT 295.T; CRL-7630: Hs 892.T; CRL-7686: Hs 936.T;CRL-7658: Hs 908.Sk; CRL-7898: A101D; CRL-7762: TE 354.T; CRL-7641: Hs 898.T; CRL-7102: Hs 156.T; CRL-7677: Hs 925.T; CRL-7806: Hs 456.T; carcinoma cells including ATTC Nos: CRL-7786: HT 756.Lu; CRL-7588: Hs 853.T; CRL-7380: Hs 618.T; CRL-7194: Hs 229.T; CRL-7209: Hs 246.T; CRL-7621: Hs 887.T; CRL-7455: Hs 717.T; CRL-7619: Hs 887.Lu; CRL-7217: Hs 266.Pe; CRL-7220: Hs 272.Pe; CRL-7796: HT 824.Pe; CRL-7873: Hs 750.T; CCL-199: HLF-a; CRL-7228: Hs 284.Pe; CRL-7906: A427; CRL-1642: LL/2; CRL-1453: KLN 205; CCL-185: A549; CCL-200: CCD-13Lu; HB-8628: L18.

Lunasin is the first antimitotic peptide whose gene has been cloned. This permitted the demonstration of its anti-mitotic and apoptosis-inducing effects when the gene is expressed in mammalian cancer cells resulting in temporary and high local concentrations of the antimitotic agent within the cancer cells. In addition, it also contains the cell adhesion motif RGD, that allows tumor cell attachment to the extra-cellular matrix (24). Synthetic and recombinant peptide analogues containing this motif prevent metastasis of tumor cells by competitive adhesion to the extracellular matrices (25). Lunasin was isolated from the water soluble and low molecular weight fraction of soybean seed proteins which had been found to have anticarcinogenic properties (26). Together with the foregoing data, this indicates that appo-priate extracellular application of lunasin, with its RGD motif, can inhibit metastasis as well as tumor growth.

Example 5

Disrupting Mitotic Function in Prostate Cancer Cells In Situ: Gene Therapy

The mammalian expression vector, pEFGP-C1 (Clon-tech), containing a Gm2S-1 peptide coding region fused at the carboxyl end of GFP is transfected by lipofectamine into three prostate cell lines: LNCap (hormone-dependent), PUC-3 (hormone independent) and ARCap (hormone-re-pressed, representing an advanced form of clinical prostate cancer (Zhau H Y E, Chang S M, Chen B Q et. al, 1996, Androgen-repressed phenotype in human prostate cancer, Proc Natl Acad Sci USA 93:15152-15157). Analagous con-structs comprising nucleic acids encoding lunasin-del, luna-sin-del-1-20, alisin, alisin-del-1-14 and Gm2S-1-syn-1-13 as described in Example 4 are similarly constructed. The green fluorescent protein (GFP) tag allows selection of transfected cells that are expressing the recombinant gene by floures-cence and phase contrast microscopy. (NSF Center for Plant Development Biology, UC Berkeley). In addition, inverted fluorescence microscopy provides monitoring in real time the progression of morphological changes in cells express-ing the various Gm2S-1 peptide-encoding constructs. Although the gene transfer efficiency is lower with pEGFP-C1, a plasmid vector, compared with viral vectors, we initially chose to use it because we can more easily select and monitor the transfected cells. This also allows us to carry out cell cycle analysis using flow cytometry (Cancer Research Lab, UC Berkeley). Chromosomal fragmentation, a hallmark of late apoptosis, is monitored with the TUNEL (terminal deoxynucleotidyl transferase (TDT)-mediated dUTP nick-end-labeling) assay using the ApoAlert DNA fragmentation assay kit from Clontech (Palo Alto,Calif.).

The basic procedure is described in Zhau et. al,1996 (supra). All the ATCC-derived prostate cell lines we are using (LNCap, PUC-3, ARCap) are known to be tumori-genic. Athymic BALB/C nude (nu/nu) mice (6-8 weeks old), congeneically inbred (Charles River Breeding Lab) are used as hosts. Stable cell lines for each of the three prostate cell lines are produced using a high-yield tetracycline-inducible retroviral vector (Retro-On Retroviral Tet System Vector, Clontech) that contains the various Gm2S-1 inserts. The resultant transformed cells are injected subcutaneously ($2\times10^6$ in 100 µl T medium per site) and tumors monitored weekly. Tumor volumes are calculated as length×width×height. The expression of the recombinant gene constructs is induced in the animals by subcutaneous injection of tetra-cycline (Clontech procedure) at an early stage and at a late stage of tumor formation. Thereafter, tumor size is moni-tored every other day. Results from these experiments dem-onstrate significant reductions in tumor volume at both early and late stages with the recited constructs except not with lunasin-del constructs.

In a second set of experiments, an adenovirus vector (Adeno-Quest from Quantum Biotechnologies Inc, (QBI, Canada) is used to introduce the Gm2S-1peptide-encoding genes into implanted prostate tumors. This receptor medi-ated mechanism provides significant positive tropism toward cells of epithelial origin, providing efficient gene transfer in both non-dividing cells and in tissue in situ through virus cell contact. Tumors are generated in the nude mice with each of the three prostate cell lines by subcuta-neous injection and tumor growth monitored as above. Recombinant replication-deficient adenovirus vectors con-taining the various Gm2S-1 inserts are constructed in Adenoquest's pQBI-pAdBM5 vector and amplified (Aden-ovirus Expression System, 1997, Quantum Biotechnologies Inc. Laval, Quebec, Canada). The inserts are cloned into the transfer vector pQBI-pAdBM5 and then transferred to the QBI-adenoviral DNA by in vivo homologous recombination in 293A human cells. The viral particles are then purified by double cesium chloride gradient purification. Purified viral particles are then introduced transcutaneously to the prostate tumors (50 µl containg $10^9$ pfu in T medium per site) in multiple injections. Tumor size is measured before injection and every other day thereafter. Results from these experi-ments also demonstrate significant reductions in tumor vol-ume at both early and late stages with the recited constructs except not with lunasin-del constructs.

Example 6

Gm2S-1 Encodes Antimutagenic Peptides

The coding regions of lunasin, alisin and the propeptides of Gm2S-1 were ligated into the bacterial expression vector, pFLAF-1 (Kodak/IBI). Bacterial transformants containing lunasin transformants showed abnormal bacterial growth and yielded 2-3× less plasmid DNA (pDNA). When the lunasin pDNAs were run on agarose gels and stained with ethidium bromide (EtBr), they were not visible under UV light, though the OD readings confirmed the presence of the pDNA. Furthermore, when treated with proteinaseK and phenol-chloroform extracted, the relaxed from of the pDNA stains readily with several DNA intercalators, including EtBr. Finally, the removal of the nine terminal aspartic acid residues of lunasin (lunasin-del) abolished this shielding effect of the peptide. These data indicate lunasin peptides can protect DNA from mutagens such as intercalating dyes. Similarly efficacy is shown with a wide variety of Gm2S-1 deletion mutants including lunasin-del-1-20 of Example 5 against a wide variety of mutagens including radionucleotides, polycyclic hydrocarbons, polychlorinated biphenyls in a number of cell types including the mammalian cell types enumerated in Example 5.

Example 7

Parenthetical References and Notes

1. L. Schweizer et al., *Proc.Natl.Acad.Sci. U.S.A.* 92, 7070 (1995); R. V. Kowles, et al., *Proc. Natl. Acad .Sci. U.S.A.* 82, 7010 (1985); D. Spencer, et al., in *Commentaries in Plant Science*, H. Smith, Ed. (Pergamon Press, New York, 1981), pp. 175-189.
2. A. J. Hauxwell et al., *Development* 110, 283 (1990).
3. A. da Silva Conceicao, E. Krebbers, *Plant J* 5, 493 (1994).
4. A. F. Galvez, M. J. R. Revilleza, B. O. de Lumen, *Plant Gene Register*, PGR97-103 in press (1997); Genbank accession number of Gm2S-1 cDNA : AF005030.
5. S. Odani, T. Koide, T. Ono, *J Biol Chem* 262, 10502 (1987).
6. Total RNAs were isolated from 200-500 mg of developing seed cotyledons and leaf tissue. Jepson et al., *Plt Mol Biol Rept* 9, 131 (1991). Northern blots were prepared using Hybond-N membrane (Amersham) R. M. Fourney et al., *Focus* 10, 5 (1988) and probed with $^{32}$P-labeled PCR fragment containing the full length Gm2S-1 coding region and a 326 bp PCR fragment of the 18S rRNA cDNA that was used as an internal control to show equal loading of total RNA in each lane. A final wash of 0.5× SSC, 0.1% SDDS at 65° C. for 15 min was performed and then blots were exposed to Hyperfilm-MP (Amersham) with intensifying screens at −80° C. for 2 days before film was developed.
7. R. Goldberg et al., *Science* 266, 605 (1994); J. A. Gatehouse et al., *Phil Trans R Soc Lond* 314, 367 (1986); D. H. Meinke et al., *Planta* 153, 130 (1981).
9. H. P. Erickson, *Trends in Cell Biol* 7, 362 (1997); H. P. Erickson et al., *Proc. Natl. Acad .Sci. U.S.A.* 93, 519 (1996); W. Margolin, R. Wang, M. Kumar, *J of Bacteriology* 178, 1320 (1996).
10. The mammalian vector used was pEGFP-C1 (Clontech). PCR amplified products containing lunasin and lunasin-del gene fragments with a 5' HindIII and a 3' EcoR1 site were generated by PCR using Gm2S-1 cDNA as template. PCR products were purified using phenol-chloroform extraction and digested with HindIII and EcoR1 before ligating by T4 ligase (Promega) to the HindIII and EcoR1 digested pEGFP-C1 vector. The pEGFP-C1 constructs were used to transform XL1-Blue competent cells and the DNA sequence verified by dideoxy sequencing (Sequenase) for in-frame ligation of lunasin and lunasin-del coding regions into pEGFP-C1.

The murine hepatoma cells (Hepa 1c1c7) were obtained from ATCC. Cells were grown in complete media (DMEM+ 10% fetal bovine serum) up to confluency ($10^7$ cells) in 10 cm plates. Cells were plated to 80% confluency overnight before transfection using electroporation. Cells were washed with PBS (1.37 mM NaCl, 2.68 mM KCl, 1.47 mM $KH_2PO_4$, 8.1 mM $Na_2HPO_4$), harvested by incubation at 37° C for 5 min with 1× trypsin/EDTA and then resuspended in complete medium at a density of 4×10$^6$. The lunasin and lunasin-del-pEGFP-C1 plasmid DNAs (pDNA) were isolated by the alkaline lysis method and 30 g of the pDNA resuspended in 20 1 PBS was added to 0.4 ml of cell suspension. Cells were incubated for 10 min at RT before they were transferred to 2 mm gap electroporation cuvette. Electroporation was done using an Electro Cell Manipulator (ECM 600, Genetronics, Inc.) using following parameters: 950 F capacitance, 72 ohms resistance and 130 V charging voltage. For flow cytometry analysis, electroporation parameters were varied from 1000-950 F capacitance and 120-150 V charging voltage. The electroporated mixture was incubated for 15 min before plating 100 1 of mixture in 4 ml of complete media in 60 mm plates. For fluorescence microscopy to assay for transient expression of GFP, sterile glass coverslips were put inside the plates. At the end of the culture period (48-80 h), cells in the coverslip were washed with PBS, incubated with 2 ml of PBS/4% paraformaldehyde for 30 min at room temperature (RT) to fix the cells, washed twice with PBS before mounting the coverslip onto a glass microscope slide with a drop of PBS. In some of the slide preparations, propidium iodide (PI) for DNA staining was added to PBS (10 ng/ml and 1 mg/ml) after cells were permeabilized by incubating with 0.2% TritonX-100 in ice for 30 min. Coverslips were attached to the glass slides with rubber cement. Phase contrast and fluorescence microscopy were done on an Axiophot microscope (Zeiss) equipped with an HBO100 mercury lamp and fluorescein (FITC) (450-490 nm exciter) and Texas Red (530-580 nm exciter) filter cubes. Images were processed using Adobe Photoshop and Canvas (Deneba) softwares.

11. Murine hepatoma cells transfected with lunasin, and the two controls, lunasin-del and pEGFP-C1 vector by electroporation (10), were prepared for flow cytometry analysis at 48 h post-transfection as follows: Cells at 50-100% confluence were washed with PBS and trypsinized. Cells were resuspended in 1.5 ml complete media and centrifuged at 3000 rpm for 3 min. Medium was aspirated and the pellet washed with 1ml cold PBS. Pellet was centrifuged at 3000 rpm for 3 min, after which PBS was removed by aspiration. Pellet was stored in −80° C. if not used immediately. For cytometry analysis, 0.5 ml of PI solution (2.5 mg propidium iodide, 50 mg Na-citrate, 50 1 TritonX-100 and 50 ml distilled water) was added to the pellet to resuspend the cells. The mixture was incubated in ice for 30 min and then filtered through a 35 m cell strain cap in a 6 ml polystyrene tube (Falcon, Franklin Lakes, N.J.). Cells were analyzed in an Epics XL-MCL Flow Cytometer (Coulter, Miami, Fla.) for PI and GFP staining. Flow cytometry data for PI staining was used for DNA content and cell cycle analysis using Multicycle AV (Phoenix Flow Systems) to determine proportion of cells at G2/M stage of cell division. Proportion of cells at G2/M in lunasin-del and pEGFP-C1-transfected cells for each transfection experiment were compared statistically using paired t-test (SigmaStat, Jandel) and found to have no significant difference ($P=0.44$). G2/M arrest in lunasin-transfected cells for each transfection experiment was computed as follows: (G2/M of GFP-lunasin transfected cells) −[(G2/M of GFP-lunasin-del transfected cells)+ (G2/M of pEGFP-C1-transfected cells)]/2. Lunasin transfection efficiency was based on flow cytometry measurements of GFP fluorescence and by counting GFP fluorescent cells in proportion to untransfected cells by fluorescence microscopy. Linear regression curve fitting between lunasin transfection efficiency and G2/M arrest was generated using SigmaPlot (Jandel) and Pearson product moment correlation coefficient was calculated using SigmaStat.
12. L. Wilson, M. A. Jordan, in *Microtubules*, J. Hyams, C. Lloyd, Eds. (Wiley-Liss Inc., New York, 1994) pp. 59-84; L. Wilson, M. A. Jordan, *Curr Biol* 2, 569 (1995).

13. The ApoAlert DNA fragmentation assay kit (Clontech) is based on the terminal deoxynucleotidyl transferase (TdT)-mediated dUTP nick-end-labeling (TUNEL) method Y. Gavrieli et al., *J Cell Biol* 119, 493 (1992); A. Facchinetti et al., *J Immunol Methods* 136, 1251 (1991). TdT incorporates fluorescein-dUTP at the free 3'-hydroxyl ends of fragmented DNA which can be visualized by fluorescence microscopy. Murine hepatoma cells transfected with lunasin and lunasin-del were grown for 24 h-72 h in plates with sterile cover slips inside to allow cells to grow on the glass cover slip. Cells were washed twice with PBS then fixed in 4% paraformaldehyde/PBS at RT for 30 min. Cells were washed twice with PBS and permeabilized by incubating with 0.2% TritonX-100 on ice for 5 min. Cells were washed with PBS twice and then covered with 100 l equilibration buffer (from Clontech kit) for 10 min at RT. TdT reaction mix was prepared as described in kit. 50 l of the TdT reaction mix was added to the cells and then allowed to incubate in a dark, humidified 37° C. incubator for 1 h. Reaction was terminated by adding 2× SSC (20×=3M NaCl, 300 mM Na-citrate) and then washed with PBS. Cells were stained by incubating in PI/RNase/PBS solution (0.5 g/ml propidium iodide, 0.5 g/l RNase) for 5 min before cover slips were mounted onto glass slides by adding a drop of antifade (1 mg/ml p-phenylenediamine, 1× PBS, 90% glycerol) and sealing the edges of the coverslip with rubber cement. Phase contrast and fluorescence microscopy were done as described (10) 14. Transfected murine hepatoma cells were allowed to grow in glass coverslips as described (10). Cells were fixed with 4% paraformaldehyde/PBS for 30 min at RT, washed twice with PBS then permeabilized by incubating in 0.2% TritonX-100 on ice for 5 min. Cells were washed twice with PBS, blocked with 3% bovine serum albumin (BSA)/PBS for 30 min then vacuum drained. A rat monoclonal antibody against a carboxy-terminal tyrosinated -tubulin epitope (YL1/2, Sera-lab) was diluted 1:200, and then added to the cells to incubate for 1 h at RT and high humidity. Cells were washed four times with 3% BSA/PBS before a fluorescein-labeled anti-rat IgG from donkey with minimal cross-reactivity (Jackson Immunoresearch) that was diluted 1:100, was added and incubated for 30 min. Cells were washed four more times before being mounted onto glass slides with antifade. Some cell preparations were stained with PI/RNase/PBS solution (13) for 5 min and then washed with distilled water before mounting. Fluorescence microscopy was done as described (10).
15. A. Nakamura et al., *J Biochem* 106, 93 (1989).
16. G. Woehlke et al., *Cell* 90, 207 (1997); J. R. McIntosh, in *Microtubules*, J. Hyams, C. Lloyd, Eds. (Wiley-Liss Inc., New York, 1994) pp. 413-434.
17. N. Hirokawa, *Curr Opin Cell Biol* 6, 74 (1994).
18. X. M. Wang et al., *J Cell Biol* 132, 345 (1996).
19. R. B. Niklas, *Science* 275, 632 (1997).
20. A. A. Hyman, E. Karsenti, *Cell* 84, 401 (1996).
21. L. D. Belmont, T. J. Mitchison, *Cell* 84, 623 (1996).
22. Human breast cancer cells (MCF-7) were plated in DMEM+10% fetal bovine serum (FBS) overnight up to 60% confluency in 60 mm plates. Harvested cells were washed with PBS twice, then trypsinized, washed and resuspended in 2 ml of serum-free media (DMEM without phenol red and FBS). Transfection was done using 8 l lipofectamine (Gibco/BRL) and 1 g of pDNA (PEGFP-C1 constructs carrying lunasin and lunasin-del (10)) that was incubated with 98 l of serum-free media for 40 min before adding to the cells. After 5 h, 2 ml of DMEM+20% FBS was added to the solution. Next day, the cells were supplied with 4 ml fresh medium (DMEM+10% FBS) and allowed to grow for 48 h before TUNEL assay was conducted as described (13). Confocal microscopy was done using a Molecular Dynamics confocal laser scanning microscope (CLSM) equipped with an argon ion laser.
23. Y. Li, R. Benezra, *Science* 274, 246 (1996).
24. E. Ruoslahti, M. D. Pierschbacher, *Cell* 44, 517 (1986); K. R. Ely et al., *Protein Engineering* 8, 823 (1995).
25. I. Hardn et al., *J Cancer* 55, 1023 (1993); J. Murata, I. Saiki *Jap J Clin Med* 53, 1653 (1995); S. K. Akiyama et al., *Cancer Metastasis Reviews* 14, 173 (1995).
26. A. R. Kennedy, *J Nutr* 125: 733S (1995); J. Yavelow et al., *Proc Natl Acad Sci USA* 82, 5395 (1985).

---

What is claimed is:

1. A method of selectively killing a human neoplastic cell, said method comprising the step of:
    administering directly at a target human neoplastic cell demonstrating undesirable mitotic function an effective amount of a nucleic acid encoding and expressing a peptide consisting essentially of 8 to 18 contiguous acidic amino acids independently selected from aspartic acid and glutamic acid residues, wherein the peptide is expressed in the target cell, and the target cell is thereby selectively killed.

2. The method of claim 1, wherein the amino acids comprise a sequence selected from the group consisting of: octa-aspartate, tetra-aspartate-tetra-glutamate, nona-aspartate, deca-aspartate, octa-glutamate, nona-glutamate, deca-glutamate, tetra(aspartate-glutamate), tri(aspartate-glutamate-aspartate), deca-(glutamate-aspartate), tetra-glutamate-tetra aspartate, tetra(glutamate-aspartate-glutamate) and tri-glutamate-penta-aspartate.

3. The method of claim 1, wherein the amino acids are Asp.

4. The method of claim 1, wherein the amino acids are present at the C-terminus of the peptide.

5. The method of claim 1, wherein the peptide comprises a basic residue on the N-terminal side of the amino acids.

6. The method of claim 1, wherein the peptide comprises residues 33-43 of SEQ ID NO:2.

7. The method of claim 1, wherein the peptide comprises residues 54-64 of SEQ ID NO:2.

8. The method of claim 1, wherein the peptide comprises residues 22-64 of SEQ ID NO:2.

9. The method of claim 1, wherein the peptide comprises at least 12 contiguous residues of SEQ ID NO:2, residues 1-35.

10. The method of claim 1, wherein the peptide comprises SEQ ID NO:2.

11. The method of claim 1, wherein the nucleic acid comprises SEQ ID NO:1.

12. The method of claim 1, wherein the cell is in situ.

13. The method of claim 1, wherein the cell is in vitro.

14. The method of claim 1, wherein the administering step comprises transfecting using a reagent selected from the group consisting of lipofectamine, a retroviral vector and an adenovirus vector.

15. The method of claim 1, wherein the target cell is selected from the group consisting of a prostate cancer cell, a breast cancer cell, a myeloma cell, a hepatic carcinoma cell, a colon carcinoma cell, a leukemia cell, an osteocarcinoma cell, a melanoma cell and a retinoblastoma cell.

16. The method of claim 1, wherein the target cell is a prostate cancer cell.

17. The method of claim 1, wherein the target cell is a breast cancer cell.

18. The method of claim 1, wherein the peptide comprises residues 22-64 of SEQ ID NO:2, and wherein the target cell is selected from the group consisting of a prostate cancer cell, a breast cancer cell, a myeloma cell, a hepatic carcinoma cell, a colon carcinoma cell, a leukemia cell, an osteocarcinoma cell, a melanoma cell and a retinoblastoma cell.

19. The method of claim 1, wherein the peptide comprises residues 22-64 of SEQ ID NO:2, and wherein the target cell is a prostate cancer cell.

20. The method of claim 1, wherein the peptide comprises residues 22-64 of SEQ ID NO:2, and wherein the target cell is a breast cancer cell.

21. The method of claim 1, wherein the peptide comprises residues 22-64 of SEQ ID NO:2, wherein the target cell is a prostate cancer cell, and wherein the administering step comprises transfecting using lipofectamine.

22. The method of claim 1, wherein the peptide comprises residues 22-64 of SEQ ID NO:2, wherein the target cell is a breast cancer cell, and wherein the administering step comprises transfecting using lipofectamine.

* * * * *

SEQUENCE LISTING (1) GENERAL INFORMATION:

(iii) NUMBER OF SEQUENCES: 3

(2) INFORMATION FOR SEQ ID NO: 1:

(i) SEQUENCE CHARACTERISTICS:
        (A) LENGTH: 770 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 1:

ACCCATCAAT AGCAAAATGA CCAAGTTCAC AATCCTCCTC ATCTCTCTTC TCTTCTGCAT     60

CGCCCACACT TGCAGCGCCT CCAAATGGCA GCACCAGCAA GATAGCTGCC GCAAGCAGC    120

CCAGGGGGTG AACCTCACGC CCTGCGAGAA GCACATCATG GAGAAGATCC AAGGCCGCG    180

CGATGACGAT GATGATGATG ACGACGACAA TCACATTCTC AGGACCATGC GGGGAAGAA    240

-continued

```
CAACTACATA AGGAGGAACG AAGGAAAAGA CGAAGACGAA GAAGAAGAAG GACACATGC      300

GAAGTGCTGC ACAGAAATGA GCGAGCTGAG AAGCCCCAAA TGCCAGTGCA AAGCGCTGC      360

GAAGATAATG GAGAACCAGA GCGAGGAACT GGAGGAGAAG CAGAAGAAGA AAATGGAGA      420

GGAGCTCATT AACTTGGCTA CTATGTGCAG GTTTGGACCC ATGATCCAGT GCGACTTGT      480

CTCCGATGAC TAAGAAGTTA AAAGCAATGT TGTCACTTGT CGTACTAACA CATGATGTG      540

TAGTTTATGC TAGCTAGCTA TAACATAAGC TGTCTCTGAG TGTGTTGTAT ATTAATAAA      600

ATCATCACTG GTGAATGGTG ATCGTGTACG TACCCTACTT AGTAGGCAAT GGAAGCACT      660

AGAGTGTGCT TTGTGCATGG CCTTGCCTCT GTTTTGAGAC TTTTGTAATG TTTTCGAGT      720

TAAATCTTTG CCTTTGCAAA AAAAAAAAAA AAAAAAAAA AAAAAAAAA                  770
```

(2) INFORMATION FOR SEQ ID NO: 2:

(i) SEQUENCE CHARACTERISTICS:
        (A) LENGTH: 158 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 2:

```
Met Thr Lys Phe Thr Ile Leu Leu Ile Ser Leu Leu Phe Cys Ile Al
 1               5                  10                  15

His Thr Cys Ser Ala Ser Lys Trp Gln His Gln Gln Asp Ser Cys Ar
            20                  25                  30

Lys Gln Leu Gln Gly Val Asn Leu Thr Pro Cys Glu Lys His Ile Me
        35                  40                  45

Glu Lys Ile Gln Gly Arg Gly Asp Asp Asp Asp Asp Asp Asp As
    50                  55                  60

Asn His Ile Leu Arg Thr Met Arg Gly Arg Ile Asn Tyr Ile Arg Ar
65                  70                  75                  80

Asn Glu Gly Lys Asp Glu Asp Glu Glu Glu Gly His Met Gln Ly
                85                  90                  95

Cys Cys Thr Glu Met Ser Glu Leu Arg Ser Pro Lys Cys Gln Cys Ly
            100                 105                 110

Ala Leu Gln Lys Ile Met Glu Asn Gln Ser Glu Glu Leu Glu Glu Ly
        115                 120                 125

Gln Lys Lys Lys Met Glu Lys Glu Leu Ile Asn Leu Ala Thr Met Cy
    130                 135                 140

Arg Phe Gly Pro Met Ile Gln Cys Asp Leu Ser Ser Asp Asp
145                 150                 155
```

(2) INFORMATION FOR SEQ ID NO: 3:

(i) SEQUENCE CHARACTERISTICS:
        (A) LENGTH: 8 amino acids
        (B) TYPE: amino acid
        (C) STRANDEDNESS: not relevant
        (D) TOPOLOGY: not relevant (ii) MOLECULE TYPE: peptide (xi) SEQUENCE DESCRIPTION: SEQ ID NO: 3:

```
Met Glu Lys Ile Gln Gly Arg Gly
 1               5
```